(12) United States Patent
Periaswamy

(10) Patent No.: US 8,472,684 B1
(45) Date of Patent: Jun. 25, 2013

(54) SYSTEMS AND METHODS FOR GENERATING FUSED MEDICAL IMAGES FROM MULTI-PARAMETRIC, MAGNETIC RESONANCE IMAGE DATA

(75) Inventor: Senthil Periaswamy, Acton, MA (US)

(73) Assignee: iCad, Inc., Nashua, NH (US)

( * ) Notice: Subject to any disclaimer, the term of this patent is extended or adjusted under 35 U.S.C. 154(b) by 463 days.

(21) Appl. No.: 12/797,231

(22) Filed: Jun. 9, 2010

(51) Int. Cl.
*G06K 9/00* (2006.01)
*G06K 9/32* (2006.01)

(52) U.S. Cl.
USPC .......................... 382/128; 382/284; 382/294

(58) Field of Classification Search
USPC ......................................... 382/128, 284, 294
See application file for complete search history.

(56) References Cited

U.S. PATENT DOCUMENTS

| | | | |
|---|---|---|---|
| 6,888,350 B2 * | 5/2005 | Deimling | 324/309 |
| 7,260,249 B2 | 8/2007 | Smith | |
| 2010/0040264 A1 * | 2/2010 | Volkau et al. | 382/128 |

FOREIGN PATENT DOCUMENTS

WO WO 2009058915 A1 5/2009

OTHER PUBLICATIONS

Ampeliotis et al. "Computer Aided Detection of Prostate Cancer using Fused Information from Dynamic Contrast Enhanced and Morphological Magnetic Resonance Images." IEEE International Conference on Signal Processing and Communications, Nov. 24, 2007, pp. 888-891.*
Garg et al. "Multilevel Medical Image Fusion Using Segmented Image by Level Set Evolution with Region Competition." 27th Annual International Conference of the Engineering in Medicine and Biology Society, Jan. 17, 2006, pp. 7680-7683.*
Vos, et al., "Computerized Analysis of Prostate Lesions in the Peripheral Zone Using Dynamic Contrast Enhanced MRI", "Med. Phys.", Mar. 2008, pp. 888-899, vol. 35, No. 3, Publisher: American Association of Physicists in Medicine.
Ocak, et al., "Dynamic Contrast-Enhanced MRI of Prostate Cancer at 3 T: A Study of Pharmacokinetic Parameters", Oct. 2007, pp. W192-W201, Publisher: American Roentgen Ray Society.
Viswanath, et al., "Integrating Structural and Functional Imaging for Computer Assisted Detection of Prostate Cancer on Multi-Protocol in V'", "Proc. of SPIE", 2009, pp. 726031-1-726031-12, vol. 7260.

(Continued)

*Primary Examiner* — Jon Chang
(74) *Attorney, Agent, or Firm* — Loginov & Associates, PLLC; William A. Loginov

(57) ABSTRACT

This invention provides a system and method for fusing and synthesizing a plurality of medical images defined by a plurality of imaging parameters that allow the visual enhancements of each image data set to be selectively combined with those of other image datasets. In this manner, a user-defined parameter set can be generated in the final response image dataset. This final response image dataset displays visual data represents a form particularly useful to the clinician. In an illustrative embodiment, the system for fusing and synthesizing the plurality of medical images provides an image fusion process/processor that fuses a plurality of magnetic resonance imaging (MRI) datasets. A first image dataset of the MRI datasets is defined by apparent diffusion coefficient (ADC) values. A second image dataset of the MRI datasets is defined by at least one parameter other than the ADC values. The image fusion processor generates a fused response image that visually displays a combination of image features generated by the ADC values combined with image features generated by the at least one parameter other than the ADC values. The fused response image can illustratively include at least one of color-enhanced regions of interest and intensity-enhanced regions of interest.

18 Claims, 10 Drawing Sheets

OTHER PUBLICATIONS

Langer, et al., "Prostate Cancer Detection With Multi-Parametric MRI: Logistic Regression Analysis of Quantitative T2, Diffusion-Weighte", "Journal of Magnetic Resonance Imaging", 2009, pp. 327-334, vol. 30, Publisher: Wiley-Liss, Inc., Published in: US.

Turkbey, et al., "Prostate Cancer: Value of Multiparametric MR Imaging at 3 T for Detection-Histopathic Correlation", "Radiology", Apr. 2010, pp. 89-99, vol. 2555, No. 1, Publisher: RSNA.

\* cited by examiner

SYSTEMS AND METHODS FOR GENERATING FUSED MEDICAL IMAGES FROM MULTI-PARAMETRIC, MAGNETIC RESONANCE IMAGE DATA

FIELD OF THE INVENTION

This application relates generally to the processing of discrete groups of medical image data. More particularly, this application relates to automated techniques for fusing and/or synthesizing medical image data acquired by imaging tissue with multiple scanning parameters, sequences, or protocols.

BACKGROUND OF THE INVENTION

Early detection of disease and malignant tissue can lead to a better prognosis. The development of non-invasive methods for detection and characterization of tumors has an extreme importance in current medicine. Magnetic resonance imaging (MRI) is a noninvasive medical test that can help physicians diagnose and treat medical conditions. MR imaging uses a powerful magnetic field, radio frequency pulses and a computer to produce detailed pictures of organs, soft tissues, bone and virtually all other internal body structures. The images can be examined on a computer monitor, printed or copied to compact disc.

By way of useful background information, according to *Breast MRI: fundamentals and technical aspects*, Hendrick, New York, N.Y.: Springer (2008), one effective breast MRI protocol for the detection and diagnosis of breast cancer has several essential elements: a non-fat-saturated T1-weighted pulse sequence, a fat-saturated $T_2$-weighted pulse sequence, and a set of contrast-enhanced pulse sequences at different phases to obtain identically acquired pre-contrast and multiple post-contrast views.

From a workflow standpoint, a clinician typically views MR image datasets by loading and outputting them to a computer, for display on a computer monitor or series of computer monitors. In this manner, the physician can visually study and manipulate the various images or "softcopies" of the images. The clinician often pre-defines a hanging protocol, which refers to the clinician's preferred arrangement of images for optimal softcopy viewing. Different clinicians might prefer to review images in different manners, depending on their experience and personal preferences. Synthesizing the information across images can be a laborious process for the clinician, especially due to the large number of thin slice images provided in each MR image dataset and the amount of spatial information in one dataset that might need to be correlated with information from one or more other datasets.

Some researchers have developed fully automated multi-modal MRI fusion techniques. By way of useful background information, one such example is described in INTEGRATING STRUCTURAL AND FUNCTIONAL IMAGING FOR COMPUTER ASSISTED DETECTION OF PROSTATE CANCER ON MULTI-PROTOCOL IN VIVO 3 TESLA MRI, by Viswanath et al, Proc. SPIE 7260, 726031 (2009). Disadvantageously, prior art fusion methods such as those described in Viswanath, provide preset solutions (e.g., fusion parameters) that are applied to all datasets regardless of the clinician's individual needs and desires and fail to integrate certain parameters of use in forming fusion images that aid clinician's in differentiating tissue types. These approaches, thus, lack both intuitiveness for a clinician and flexibility in adapting to a clinician's specific protocol.

SUMMARY OF THE INVENTION

This invention overcomes disadvantages of the prior art by providing a system and method for fusing and synthesizing a plurality of medical images defined by a plurality of imaging parameters that allow the visual enhancements of each image data set to be selectively combined with those of other image datasets. In this manner, a user-defined parameter set can be generated in the final response image dataset. This final response image dataset displays visual data represents a form particularly useful to the clinician. In an illustrative embodiment, the system for fusing and synthesizing the plurality of medical images provides an image fusion process/processor that fuses a plurality of magnetic resonance imaging (MRI) datasets. A first image dataset of the MRI datasets is defined by apparent diffusion coefficient (ADC) values. A second image dataset of the MRI datasets is defined by at least one parameter other than the ADC values. The image fusion processor generates a fused response image that visually displays a combination of image features generated by the ADC values combined with image features generated by the at least one parameter other than the ADC values. The fused response image can illustratively include at least one of color-enhanced regions of interest and intensity-enhanced regions of interest.

In an illustrative embodiment, the at least one parameter can be based upon at least one of a $T_2$-weighted medical image and a dynamic contrast enhanced MRI (DCE-MRI) medical image. A registration process/processor can be provided. It aligns each of the first image data set and the second image dataset into a registered multi-modal image dataset. This registration process/processor can also illustratively include a non-rigid registration process/processor and an atlas/template processor that operates upon the image data based upon atlas coordinate data related to imaged tissue. In an embodiment, a segmentation process/processor is provided to apply organ/tissue atlas coordinate data to the registered multi-modal image dataset to generate segmented organ/tissue image data with respect to regions of interest in the multi-modal image dataset. Additionally, an intensity homogeneity correction process/processor can be provided to generate a homogeneous organ/tissue image dataset by smoothing and filtering image intensities with respect to the organ/tissue image data.

In an embodiment, the fusion process/processor receives inputs of user-defined parameters to vary image data displayed in the fused response image in accordance with the user's desired criteria. These criteria can be input in advance of any processing of the image data, or during image processing operations. The user can visually observe how the variation of parameters changes the output results, and adjust the user-defined parameters accordingly during runtime of the system. The fusion process/processor can further include (a) a scale normalizing process/processor that receives map data from a multi-modal parameter source and generates scale-normalized parameter values and (b) a response process/processor that generates response values that define the fused response image.

In another embodiment, a system and method for fusing and synthesizing a plurality of medical images defined by a plurality of imaging parameters includes an image fusion process/processor that fuses a plurality of magnetic resonance imaging (MRI) datasets, in which a first image dataset of the MRI datasets is defined by at least a first parameter and a second image dataset of the MRI datasets is defined by at least a second parameter. The image fusion process/processor generates a fused response image that visually displays a combination of image features from the first image dataset and image features from the second image dataset based upon user defined parameters input to the image fusion process/ processor through a user interface prior to operation of the image fusion process/processor to generate the fused response image.

In yet another embodiment, a system and method for fusing and synthesizing a plurality of medical images defined by a plurality of imaging parameters includes an image fusion process/processor that fuses a plurality of magnetic resonance imaging (MRI) datasets, in which a first image dataset of the MRI datasets is defined by morphology values and a second image dataset of the MRI datasets is defined by at least one parameter other than the morphology values. The image fusion process/processor generates a fused response image that visually displays a combination of image features from the first image dataset and image features from the second image dataset.

In yet another embodiment, a system and method for fusing and synthesizing a plurality of medical images defined by a plurality of imaging parameters includes an image fusion process/processor that fuses a plurality of magnetic resonance imaging (MRI) datasets. The image fusion process/processor generates a fused response image that visually displays a combination of image features from the first image dataset and image features from the second image dataset. Illustratively a segmentation processor, in communication with the image fusion processor, generates corresponding segments of each of the first image dataset and the second image data set based upon predetermined segmenting data so that each of the segments, so that the corresponding segments are each discretely fused by the image fusion processor.

BRIEF DESCRIPTION OF THE DRAWINGS

The invention description below refers to the accompanying drawings, of which.

DETAILED DESCRIPTION

In the present disclosure, the terms "pixels" and "voxels" can be used interchangeably to refer to an element in an image. Image data is generally represented in units of picture elements (pixels). A pixel generally refers to the information stored for a single grid in an image or a basic unit of the composition of an image, usually in a two-dimensional space, for example, x-y coordinate system. Pixels can become volumetric pixels or "voxels" in three-dimensional space (x, y, z coordinates) by the addition of at least a third dimension, often specified as a z-coordinate. A voxel thus refers to a unit of volume corresponding to the basic element in an image that corresponds to the unit of volume of the tissue being scanned. It should be appreciated that this disclosure can utilize pixels, voxels and any other unit representations of an image to achieve the desired objectives presented herein. Both pixels and voxels each contain a discrete intensity and/or color, which is typically defined as one or more digital values within a given range (for example, a grayscale intensity between 0 and 255, or discrete RGB values each between 0 and 255).

Also in the present disclosure, the terms "image", "dataset" and/or "image dataset" can be used interchangeably to refer not just to a single image, but to an n-dimensional plurality of images. These images can take the form of a volume of images, a plurality of volumes, or even a plurality of datasets. By way of example, in dynamic, contrast-enhanced magnetic resonance imaging (DCE-MRI), a plurality of slice images is typically acquired before, during, and after contrast agent infusion, resulting in the acquisition of a time sequence of image volumes. In this example, the terms "image", "dataset" and/or "image dataset" can be used to refer to a plurality of slice images of the tissue at a given time point, a plurality of slices images of the tissue across different time points, or a plurality of image volumes of the tissue across different time points.

Figure 1:
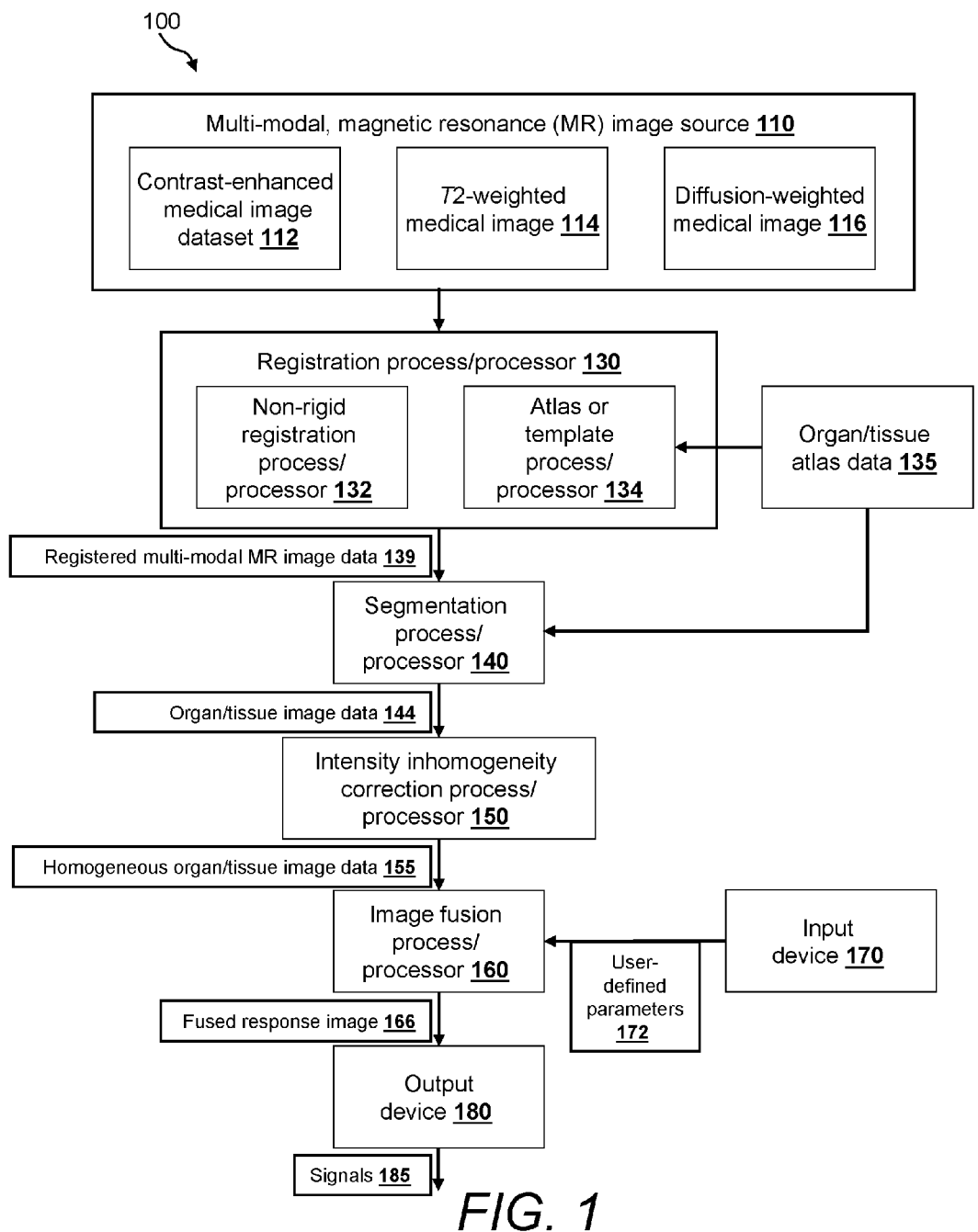
FIG. 1 is a block diagram of an illustrative embodiment of an image processing system.

With reference to FIG. 1, there is shown a block diagram of components of an image processing system 100 according to an illustrative embodiment. Processor blocks shown within the system illustrate different image processing functions that can be performed on medical image data. Such functions can be realized by suitable combinations of hardware and software components ("software" being defined herein as a computer-readable medium of program instructions) of the image processing system such as, but not necessarily limited to, microprocessors, digital signal processors (DSPs), field-programmable gate arrays (FPGAs), main memories, secondary/auxiliary memories, input/output devices, operating system software, application software, etc. Any such functions, either entirely or in part, can be further implemented on such a computer-readable medium/media that can be read by the system to achieve the desired objectives presented herein. Note that while the process functions herein are assigned to discrete processor blocks by way of illustration, it is expressly contemplated that functions of various blocks can be consolidated, expanded to further processor blocks or reordered between blocks as appropriate to carry out the overall process described herein.

The image processing system 100 includes a multi-modal, magnetic resonance (MR) image source 110 for acquiring and/or storing multi-modal MR image data. In certain embodiments, the image source 110 includes or comprises an MR scanner apparatus (not shown) that generates images using different magnetic resonance scanning parameters, which are also referred to as sequences, protocols, or scans. An advantage offered by MRI is the ability to capture tissue information using different protocols within the same acquisition. In other expressly contemplated embodiments, the image source includes, or comprises, previously acquired images saved in an electronic memory or computer-readable storage medium, such as a computer memory, random access memory (RAM), solid state memory (e.g. compact flash), electro-optical disk storage, magnetic tape or magnetic disk storage, etc. Illustratively, the image source can be a Picture Archiving and Communication System (PACS) for storing, retrieving, and distributing medical image data between components of the image processing system. Alternatively, any directly attached or networked storage device with appropriate data organization can be employed to store, and allow retrieval of, the image data. For example, the storage device can comprise a removable disk or solid-state storage, a network-attached-storage appliance, a storage area network (SAN) and/or a remote data store accessed by a secure private network, such as a hospital wide area network or a public network. Appropriate layers of encryption can be applied to the transmitted as well as the stored data as required to satisfy various governmental and institutional security requirements. Such encryption techniques should be clear to those of ordinary skill.

In one embodiment, the image source provides a contrast-enhanced medical image dataset 112, a $T_2$-weighted medical image 114, and a diffusion-weighted medical image 116. The source can provide additional or alternative multi-modal MR medical image data. Other explicitly contemplated embodiments include, without limitation, $T_1$-weighted non-fat-saturated medical images and/or MR spectroscopy medical images. The illustrative medical images provided by the source form a "study" or a "case" of organs or tissues under study. Individually, each medical image can provide some visual distinction between different tissue types (e.g., malignant or benign). However, some tissue types can only be discerned using one particular source of image. It has been observed that the signature of some tissue types is also more apparent when examining the image information available through a study. The exemplary medical images 112, 114, and 116 will now be briefly introduced by way of illustration.

Dynamic Contrast Enhanced Magnetic Resonance Imaging (DCE-MRI)

In dynamic, contrast-enhanced magnetic resonance imaging, or DCE-MRI, the increased permeability of tumor vasculature gives rise to increased leakage of tracers such as a contrast medium, which can be administered to a patient by intravenous injection, or another suitable infusion technique. The contrast medium can be any media/agent useful in distinguishing tissue types such as, but not limited to, a gadolinium-based contrast agent. In DCE-MR imaging, a stream of contrast-enhanced medical image datasets 112 is acquired at predetermined time intervals (typically before, during, and after the contrast agent infusion) defined by "dynamic phases." The stream therefore enables characterization of visual enhancement patterns in the tissue. By comparing images taken before and after contrast material injection, a contrast-enhanced study can help to determine if an anatomical region under study contains abnormalities, whether an abnormality appears benign (non-cancerous) or malignant (cancerous), and the size and location of any abnormality that appears malignant. It is noted that contrast-enhanced medical image datasets can be acquired using a computed tomography (CT) scanner, in which case the source 110 (FIG. 1) can include or comprise a CT scanner apparatus to illustratively acquire this portion of the multi-modal MR image data.

$T_2$-Weighted MRI

Another MRI sequence of interest is a $T_2$-weighted ($T_2$-w) MRI scan. By way of useful background information, $T_2$-w MRI scans use a spin echo (SE) sequence with a long echo time (TE) and repetition time (TR) to suppress imaging of body fat. As a result, different tissue types often exhibit different signal intensity values on $T_2$-w medical images 114. For example, cysts typically appear visually much brighter than other breast tissue. Another advantage of the $T_2$-w MRI scan is that the tissue can be imaged at a higher spatial image resolution than other sequences.

Diffusion-Weighted MRI

By way of useful background information, diffusion-weighted MR pulse sequences measure the apparent diffusion coefficient (ADC) of water in tissue. Each voxel of a diffusion-weighted image has a signal intensity that reflects a single best measurement of the rate of water diffusion at that location. An ADC value associated with each voxel is illustratively computed from a plurality of intensity signals generated by repeating the diffusion-weighted pulse sequence multiple times. Illustratively, ADC values can be computed and/or provided directly by the source 110 along with the diffusion-weighted medical image 116.

In an embodiment, the image processing system 100 includes a registration process/processor 130 that registers multi-modal MR images both intra-("within") and inter-("across") modality. Such transformations can be required due to deformation of the organ or tissue of interest during image acquisition and/or across imaging sequences. Breathing and patient movements are two sources of potential deformation. In certain embodiments, the registration process/processor includes a non-rigid registration process/processor 132 for performing intra-modality registration and an atlas or template registration process/processor 134 for performing inter-modality registration. In accordance with further embodiments, the atlas registration process/processor reads organ/tissue atlas coordinate data (also termed, simple "atlas data") 135 from memory and uses the atlas data to successfully register the images. The atlas data contains a DCE-MR atlas, a $T_2$-weighted atlas, and a diffusion-weighted atlas. Each atlas represents a-priori knowledge about the shape of the anatomical region in the corresponding sequence. In other embodiments, in which the source 110 provides other medical images, different atlases are provided instead of, or in addition to, those described herein. Illustratively, the stored atlases are pre-registered to one another via an offline registration process, which provides advantages during the inter-modality registration runtime procedure. By the transitive property of equality, once each individual image is registered with respect to its stored atlas, all multi-modal images acquired from the source are then registered inter-modality. The output from the registration processor is illustratively shown as registered multi-modal MR image data 139.

In other contemplated embodiments, the registration process/processor 130 exclusively includes the non-rigid registration process/processor 132 that individually registers each medical image 112, 114, and 116 to a single baseline/reference image. Illustratively, the baseline/reference image used by the process/processor can be a pre-contrast volume (i.e., before contrast injection, also referred to as $t_0$) within the contrast-enhanced, medical image time series 112. All other image volumes, including post-contrast volumes of the contrast-enhanced time series, are then registered to the baseline/reference image to form the registered image data 139.

Figure 2:
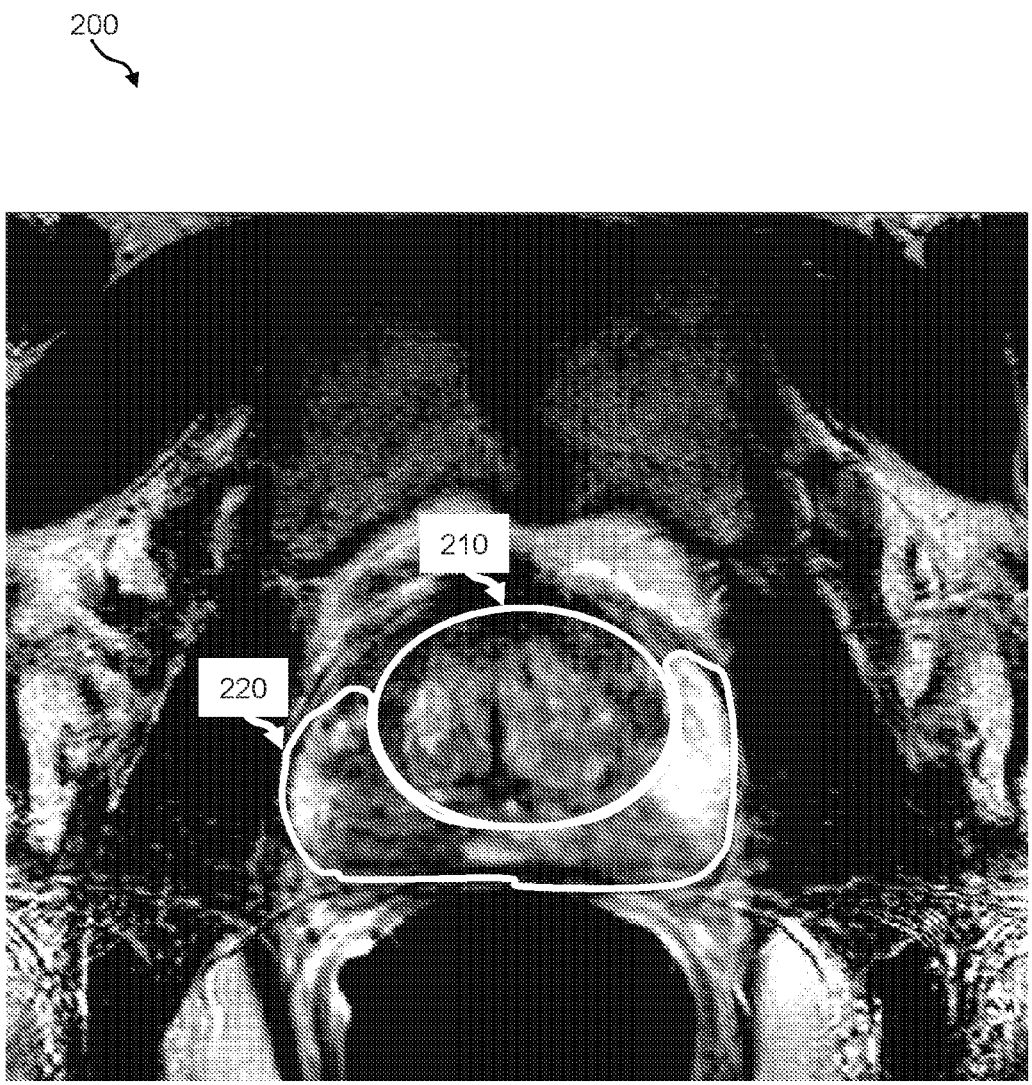
FIG. 2 is a depiction of illustrative anatomical regions or zones of a prostate that can be segmented and processed using the image processing system of FIG. 1.

In an embodiment, the image processing system 100 includes a segmentation process/processor 140 that automatically segments organ/tissue data of interest 144 from background. Examples of background data can include air, noise, or other tissue that is outside the field of view, whereas examples of organ/tissue data of interest can include a patient's breast or breasts, lung or lungs, liver, prostate, etc. In accordance with certain embodiments the organ/tissue data of interest can be further segmented into distinct regions or zones, which has the advantage of enabling a region-based or "local" implementation of multi-modal parametric fusion to be further described herein below. For example, in embodiments in which the image source 110 provides multi-modal images of the prostate and surrounding regions, FIG. 2 illustrates exemplary runtime results when the segmentation process/processor 140 is configured to segment a central/transition zone (depicted by reference numeral 210) and a peripheral zone (depicted by reference numeral 220) from prostatic images. In other explicitly contemplated examples and embodiments, the segmentation process/processor can segment a prostate peripheral zone, a prostate central gland/zone, a prostate transition zone, and prostate seminal vesicles from the image. In one embodiment, the segmentation process/processor 140 automatically segments prostatic images into such illustrative zones using pre-labeled segmentations provided in the organ/tissue atlas data 135. An example of an atlas-based registration/segmentation that can be performed by the registration and segmentation processes/processors is described by Gubern-Merida et al. in "Atlas Based Segmentation of the prostate in MR images," *International Conference on Medical Image Computing and Computer Assisted Intervention (MICCAI): Segmentation Challenge Workshop, London, 2009*," available through the World Wide Web of the well-known Internet at the URL address, wiki.na-mic.org/Wiki/images/d/d3/Gubern-Merida_Paper.pdf. It is expressly contemplated that other image processing segmentation techniques can be implemented in the segmentation process/processor 140.

Note, as used generally herein the terms "automated," "automatic" and "automatically" should be taken to mean operations that are substantially or completely free of human effort in their performance. Such processes are potentially initiated or have parameters set by human effort, or by another automated process or apparatus, but thereafter proceed with minimal or no human effort. It is contemplated that, at certain time points, the automatic process can request human guidance, but the primary work performed in computing and handling data is performed by the process using, for example hardware and/or software. For example, human effort directs the system to begin fusing image data and at subsequent times, the system, after performing some or all of the fusion, requests the human operator to enter a location to store or display the results.

In an embodiment, the image processing system 100 (FIG. 1) includes an intensity inhomogeneity correction process/processor 150 that corrects medical images for intensity inhomogeneity artifacts occurring as a result of non-homogeneous magnetic fields during image acquisition. By way of background, subtle variations in the strength of the applied magnetic field with respect to location can typically occur. The applied magnetic field can also vary with respect to time. The effect of the inhomogeneous magnetic field can result in uneven enhancement throughout portions of the image that should otherwise appear uniform. This unevenness can adversely affect further post-processing of the images. For example, in the contrast-enhanced medical images 112, the variations in the magnetic field can falsely simulate the appearance of signal enhancement over time. One algorithm suitable for implementation in the intensity inhomogeneity correction processor is described by way of useful background in Salvado, et al., in "Method to correct intensity inhomogeneity in MR images for atherosclerosis characterization," *IEEE Trans Med Imaging*, 2006 May; 25(5):539-52. It is expressly contemplated that other algorithms may also be implemented in the intensity inhomogeneity correction process/processor. The output from the processor is illustratively shown as homogeneous multi-modal MR image data 155.

The image processing system 100 further includes an image fusion process/processor 160 that generates a fused response image or map 166 from the multi-modal MR image data. For purposes of this description, the fused response image can also be defined generally as a "probability map" or "color map." Briefly, "image fusion" as used herein can be defined as a process of combining raw image data, post-processed image data, or combinations thereof from two or more images acquired using different medical imaging (e.g., magnetic resonance) scanner parameters (i.e., sequences, protocols, scans) into a single image. The "response image," "probability map," and "color map" are examples of singular images that visually illustrate data resulting from an image fusion process. The single image thereby provides an important diagnostic output tool for a clinician, as it synthesizes a large amount of spatial, temporal, and functional tissue data in an objective manner. This tool enables a clinician to quickly and easily visualize tissue pixels, voxels, or regions of potential interest without necessarily having to review an entire case of MR images, which can be a time-consuming, subjective, and error-prone process. Exemplary processes by which the image fusion processor can generate the fused response image are further described herein below.

In an embodiment, the image processing system 100 is connected to an input device 170, and enables a user-defined implementation of multi-modal parametric fusion. The input device can be a keyboard, a mouse unit, a touch screen/touchpad, a voice-activated input device, or other suitable device that can be conventional or customized in a manner clear to those of skill in the art. The system receives a set of user-defined parameters 172 via the input device. The parameters 172 are illustratively stored in memory (not shown in FIG. 1) in the processing system, and transmitted to the image fusion process/processor 160 at runtime to be operated upon in the generation of a desired output response image. It is expressly contemplated that the user-defined parameters can also be received in a flat file, database or other suitable data structure via a network connection (not shown in FIG. 1) from other systems, allowing different clinicians to remotely share and implement different fusion parameters.

It can be desirable to enable human users to input parameters to be used in the multi-modal MR image fusion procedure so as to achieve a variety of goals. There is no universally accepted way in the medical community for clinicians to combine and evaluate MRI datasets acquired with different sequences. As discussed in the background, different clinicians possibly prefer to evaluate images in different manners. Experimentation with different types, weights and combinations of input parameters can enable clinicians to discover optimal parameters for computing novel response images. For example, one set of input weights can be used for creating response images optimal for distinguishing malignancy tissue from benign tissue. Another set of input weights can be used for creating response images optimal for identifying a particular type of malignant tissue, such as ductal carcinoma in situ ("DCIS") breast cancers. Another set of input weights can be used for creating response images optimal for identifying cancer in a particular region of an organ. Furthermore, experimentation with and modifications to input parameters can be desirable, or required, as changes to MRI protocol and sequences are made to the clinician's MR image acquisition protocols.

Another component of the image processing system 100 is an output device 180. The output device can comprise a printer, a computer monitor, a series of computer monitors, and/or other suitable signal output devices of conventional or novel design that generate one or more viewable images. The output device could also be a compact disc, disk drive and/or another suitable storage medium/device that allows image data to be stored, accessed and output. The output device enables signals 185 to be output in many forms suitable for visual inspection of the tissue including, without limitation, raw images 112, 114, and/or 116 acquired by the source 110 and fused response images 166 produced by the image fusion process/processor 160.

It is expressly contemplated that components of the image processing system 100 can connect to and communicate with each other via one or more of any type or combination of types of communication interfaces, including but not limited to physical interfaces, network interfaces, software interfaces, and the like. The communication can be implemented using a physical connection, and/or wireless, optical, or any other medium. Alternatively, image datasets and/or fused response images can be transmitted indirectly by use of transportable storage devices (not shown in FIG. 1) such as but not limited to portable compact discs (CDs), digital video discs (DVDs), or solid state "flash" drives, in which case readers for said transportable storage devices can function as communication interfaces of the system.

Runtime Operation of the System

In operation, and with further reference to FIG. 1 which will be used to describe the steps in a runtime procedure, the contrast-enhanced medical image 112, the $T_2$-weighted medical image 114, and the diffusion-weighted medical image 116 are acquired from the source 110, and loaded into a system image memory for processing. In a next step, the non-rigid registration process/processor 132 registers the volumes of the contrast-enhanced, medical image 112. The atlas registration processor 134 then reads the organ/tissue atlas data 135 from memory and individually registers the intra-registered contrast-enhanced medical image, $T_2$-weighted medical image, and diffusion-weighted medical image to their respective stored, pre-registered atlases. After the registration step, the tissues and/or organs in the multi-modal MR images are considered aligned in a single coordinate system. In a next step, the segmentation processor/processor 140 applies prelabelled image coordinates of the organ/tissue atlas data 135 to each registered image as a mechanism to automatically detect and segment the organ/tissue of interest 144. Optionally, the organ data is further segmented into distinct regions or zones. This can allow focus on a particular area or areas of the tissue that is of specific interest to the clinician. In a further optional procedure, the intensity inhomogeneity correction process/processor 150 corrects non-homogenous image intensities of the segmented organ/tissue of interest data or subsets thereof. This can be performed using conventional image smoothing and filtering techniques, among other image processing applications. In alternate embodiments, the order of the steps of registration, segmentation and intensity inhomogeneity image pre-processing can be varied. For example, intensity inhomogeneity correction can be performed prior to registration or segmentation. In the next step, the pre-processed image data is then transmitted to the image fusion process/processor 160 for computation of the fused response image 166, examples of which are referenced in detail herein below.

Image Fusion Process/Processor

Figure 3:
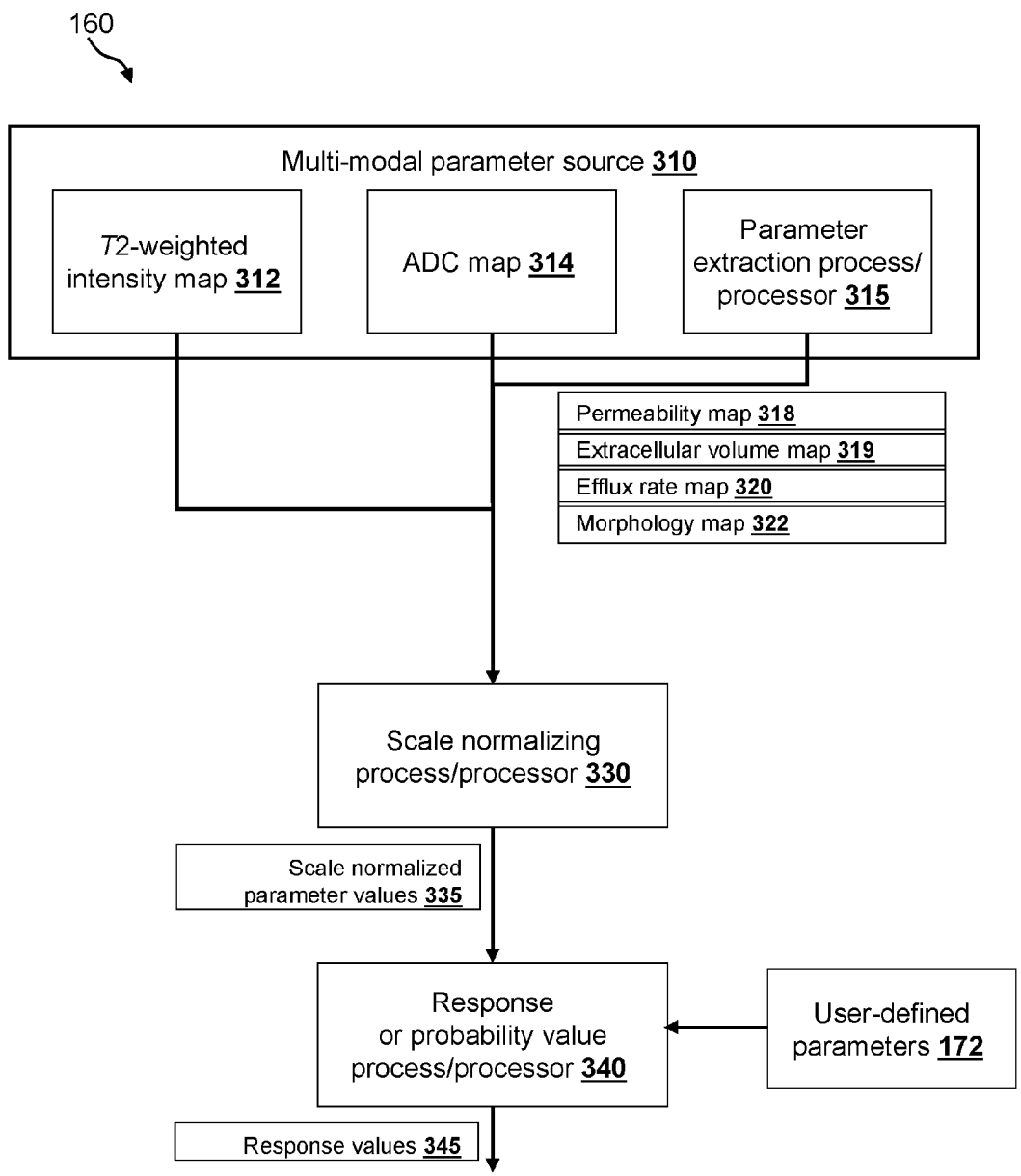
FIG. 3 is a block diagram of an illustrative embodiment of an image fusion process/processor for use with the image processing system of FIG. 1.

With reference now to FIG. 3, a block diagram of an illustrative embodiment of the image fusion process/processor 160 is shown. With reference also to FIG. 1, the inputs are pre-processed representations (e.g., registered, segmented, inhomogeneous intensity corrected) of the images 112, 114, and 116 to be fused. In embodiments of a user-defined implementation of the fusion process, user-defined parameters 172 are also acquired as inputs. The output is the fused response image and/or the probability map 166 of computed response values.

The image fusion process/processor 160 includes a multi-modal parameter source 310 for acquiring and/or storing multi-modal parameter values or features to be used in fusion computations. In certain embodiments, raw values of some or all of the input images are provided as parameter values. The input images can be smoothed before fusion to remove noise and/or provide more continuous parameter values. Illustrative examples of parameter values include a $T_2$-weighted intensity map 312 and an ADC map 314. Examples are visually illustrated in FIGS. 4 and 5. "Map" or "parametric map" as used herein refers to a representation of parametric feature values associated with the pixels or voxels of an image.

Figure 4:
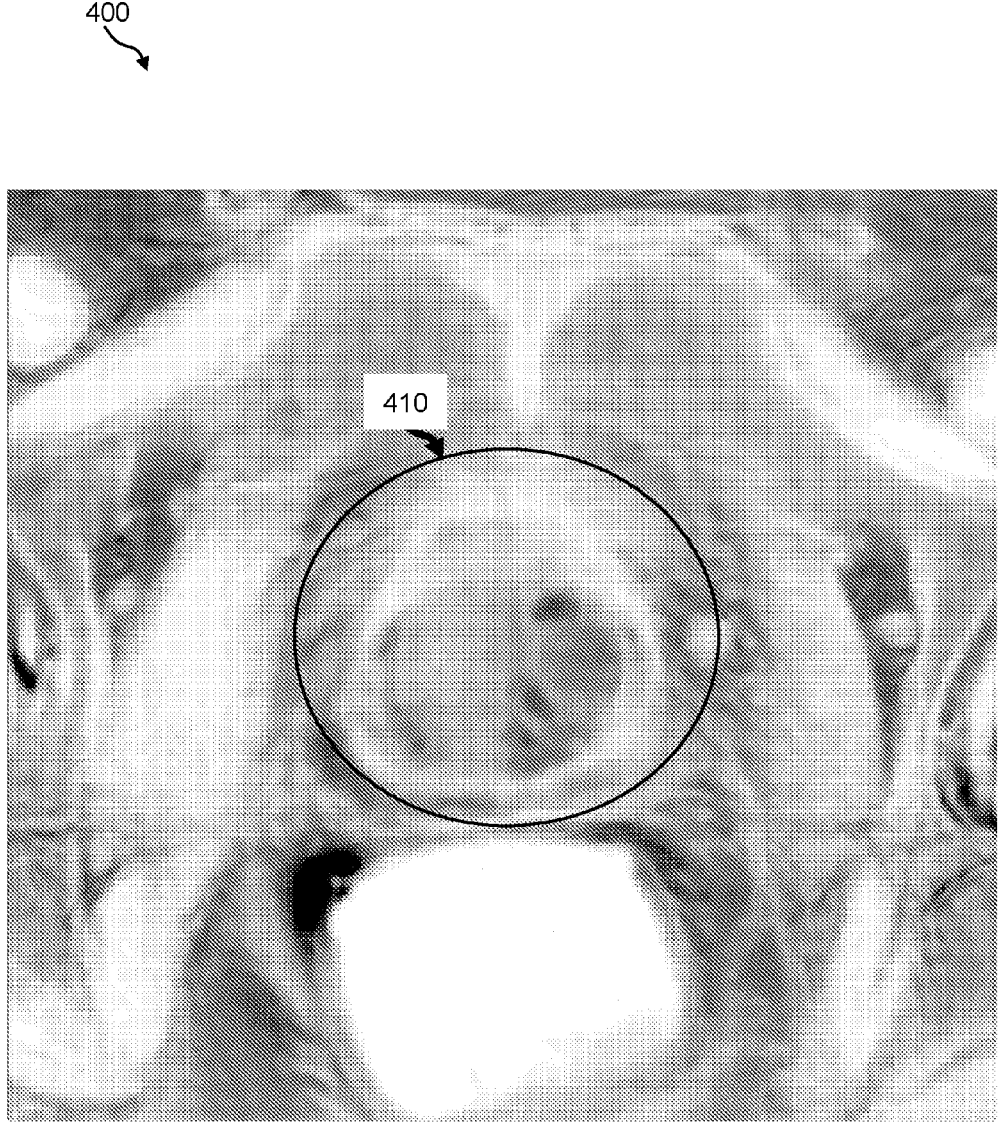
FIG. 4 is a depiction of an exemplary $T_2$-weighted intensity map that can be acquired and processed using the image fusion process/processor of FIG. 3.

FIG. 4 provides an exemplary $T_2$-weighted intensity map 400 that was derived by smoothing, scaling, and inverting a $T_2$-weighted image of a prostate 410 and surrounding regions in accordance with illustrative operational steps to be further described herein below. Using these inverted maps, the image fusion process/processor 160 can provide a greater emphasis in tissues that exhibit high signal intensity values. In this example, within the general region of the prostate, although differences in signal intensity values can be observed, there appears to be no conclusive indication of a region of interest.

Figure 5:
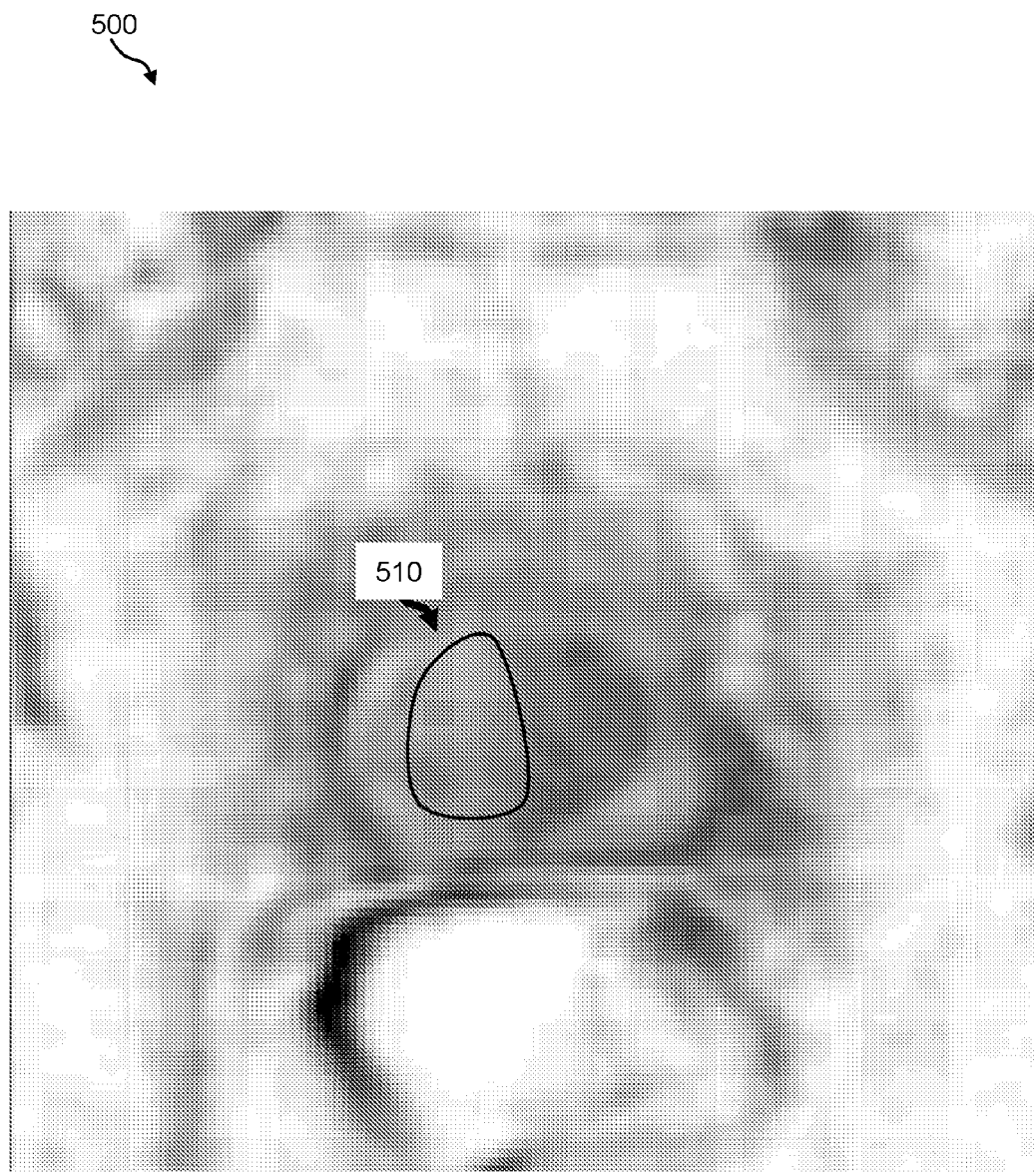
FIG. 5 is a depiction of an exemplary apparent diffusion coefficient (ADC) map that can be acquired and processed using the image fusion process/processor of FIG. 3.

FIG. 5 provides an exemplary ADC map 500 that was derived by smoothing, scaling, and inverting a diffusion-weighted image of the same prostate depicted in FIG. 4 in accordance with illustrative operational steps to be further described herein below. Using these inverted maps, the image fusion process/processor 160 can provide a greater emphasis in tissues that exhibit high signal intensity values. In this example, note a cluster of pixels depicted by the reference numeral 510 that appear to be a potential tissue region of interest, as the clusters appear to be quite light relative to surrounding tissues in the prostate central/transition zone. Referring back to the $T_2$-weighted intensity map 400, only a slight difference between intensities can be observed in this region with respect to other prostate tissues.

In certain embodiments of the image fusion process/processor 160 as shown in FIG. 3, the parameter source 310 optionally includes or comprises a parameter or feature extraction process/processor 315 that extracts parametric values from some or all of the multi-modal input images. Illustratively, physiological or kinetic tissue parameters can be extracted by applying a known pharmacokinetic model (e.g., Tofts model) to the pixel signal intensity values of the pre-processed, contrast-enhanced medical image dataset. Exemplary kinetic tissue parameters that can be extracted from such imagery include a transfer constant or permeability surface ($k_{trans}$) map 318, an extracellular volume ($v_e$) map 319, and/or an efflux rate constant ($k_{ep}$) map 320, examples of which are visually illustrated as derived images or maps in FIGS. 6, 7, and 8, respectively. In one embodiment, the parameter extraction process/processor 315 automatically computes such kinetic tissue parameters as described by Tofts et al., in "Estimating kinetic parameters from dynamic contrast-enhanced T(1)-weighted MRI of a diffusable tracer: standardized quantities and symbols," *J Magn Reson Imaging*, 10 (3). pp. 223-232.

Figure 6:
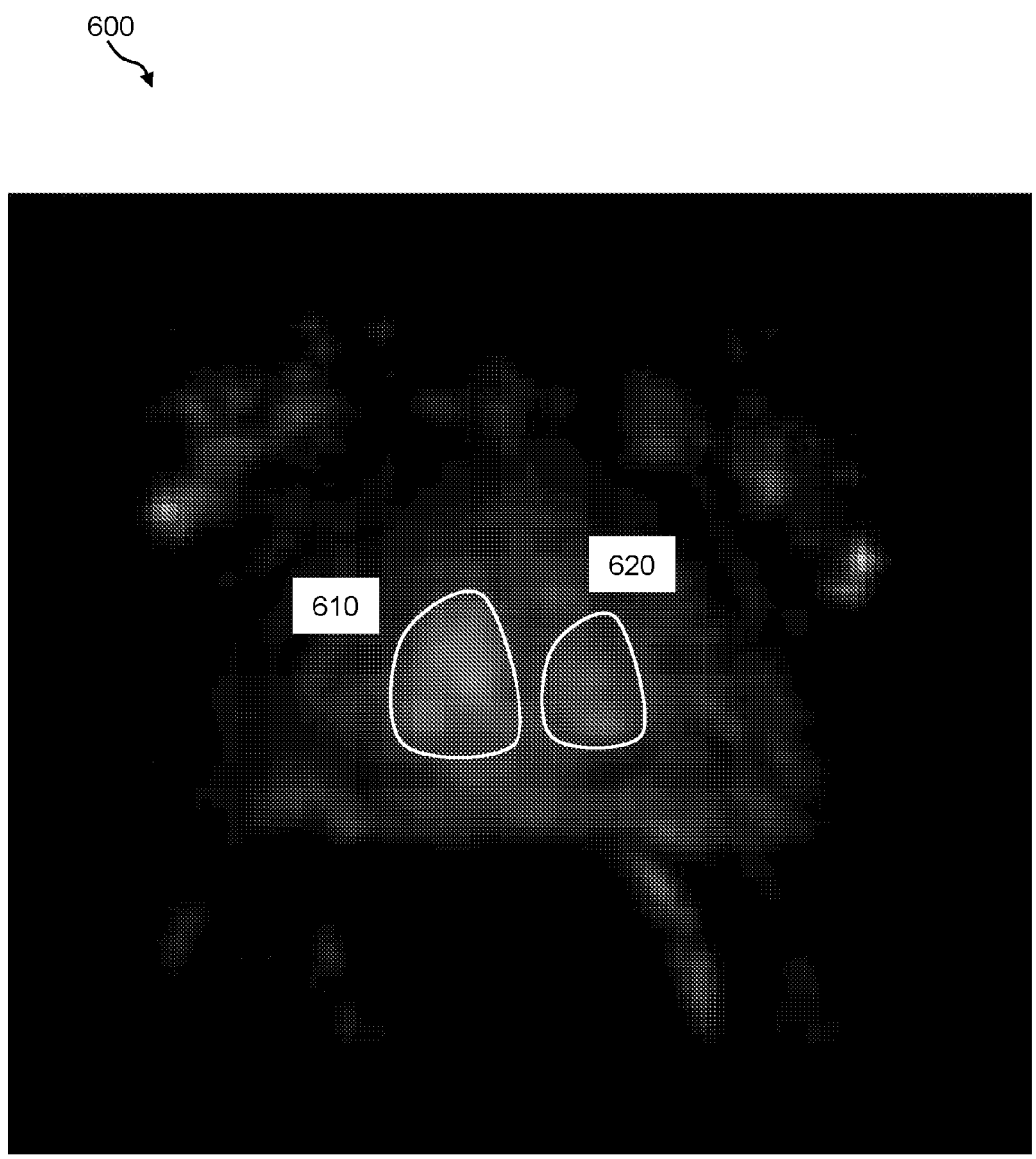
FIG. 6 is a depiction of an exemplary permeability map that can be acquired and processed using the image fusion process/processor of FIG. 3.

FIG. 6 provides an exemplary smoothed permeability map 600 that has been derived by computing permeability parameters from a contrast-enhanced dataset of the same prostate depicted in FIGS. 4-5 in accordance with an embodiment. Using these maps, the image fusion process/processor 160 can provide a greater emphasis in tissues that exhibit high signal intensity values. In this example, the reader should note two clusters of pixels depicted by the reference numerals 610 and 620 that appear to be potential regions of interest, as the clusters exhibit strong intensities. While cluster 620 has failed to exhibit interesting signatures in both the $T_2$-weighted intensity and ADC maps, cluster 610 appears to be the same potential tissue region of interest as the cluster 510 in ADC map 500.

Figure 7:
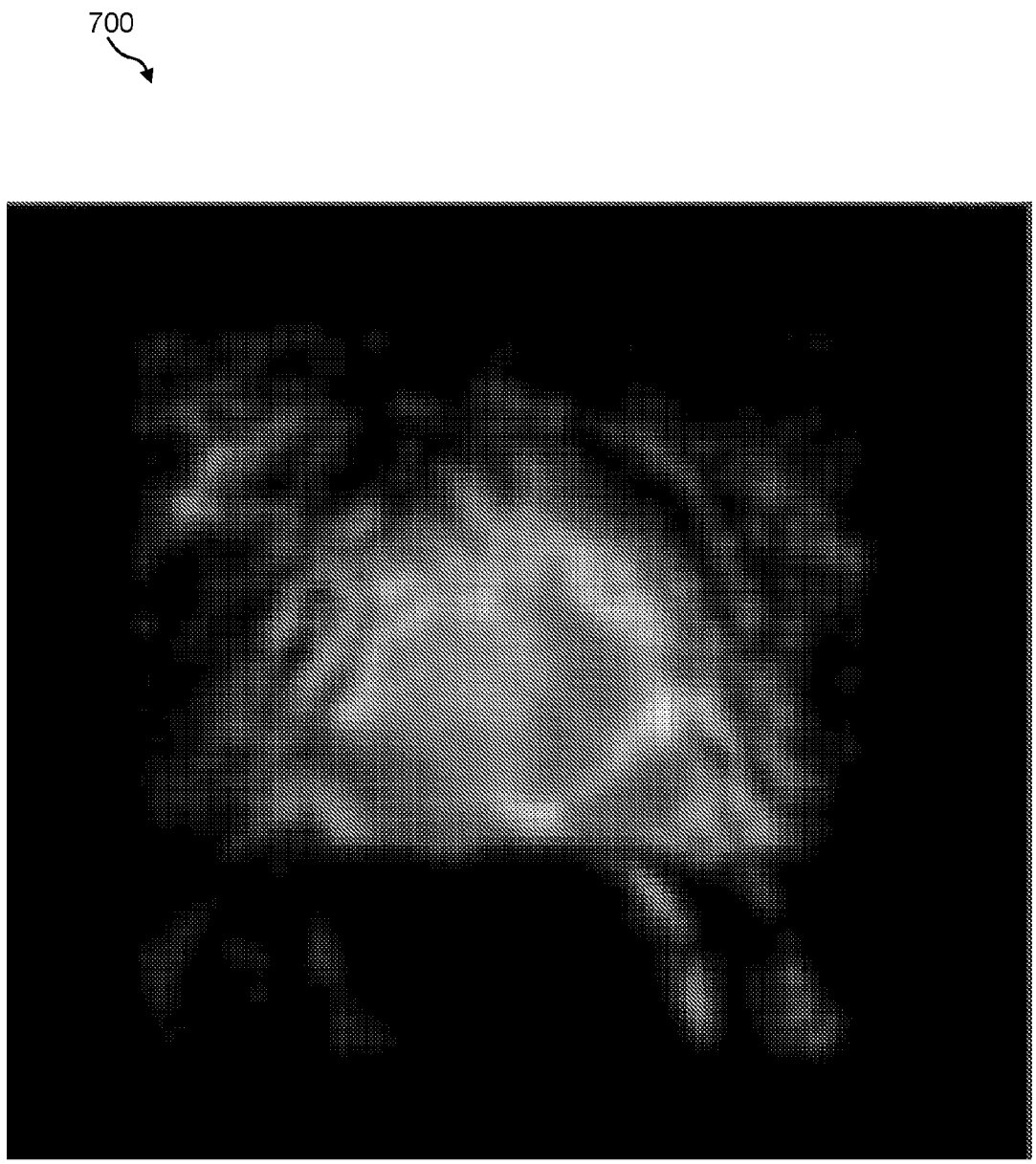
FIG. 7 is a depiction of an exemplary extracellular volume map that can be acquired and processed using the image fusion process/processor of FIG. 3.

FIG. 7 provides an exemplary smoothed extracellular volume map 700 that has been derived by computing extracellular volume parameters from a contrast-enhanced dataset of the same prostate depicted in FIGS. 4-6. Using these maps, the image fusion process/processor 160 can provide a greater emphasis in tissues that exhibit high signal intensity values. In this example, within the general region of the prostate, there appears to be no conclusive indication of a region of interest, although tissues on the left side of the prostate central/transition zone do appear to be lighter relative to tissues on the right side.

Figure 8:
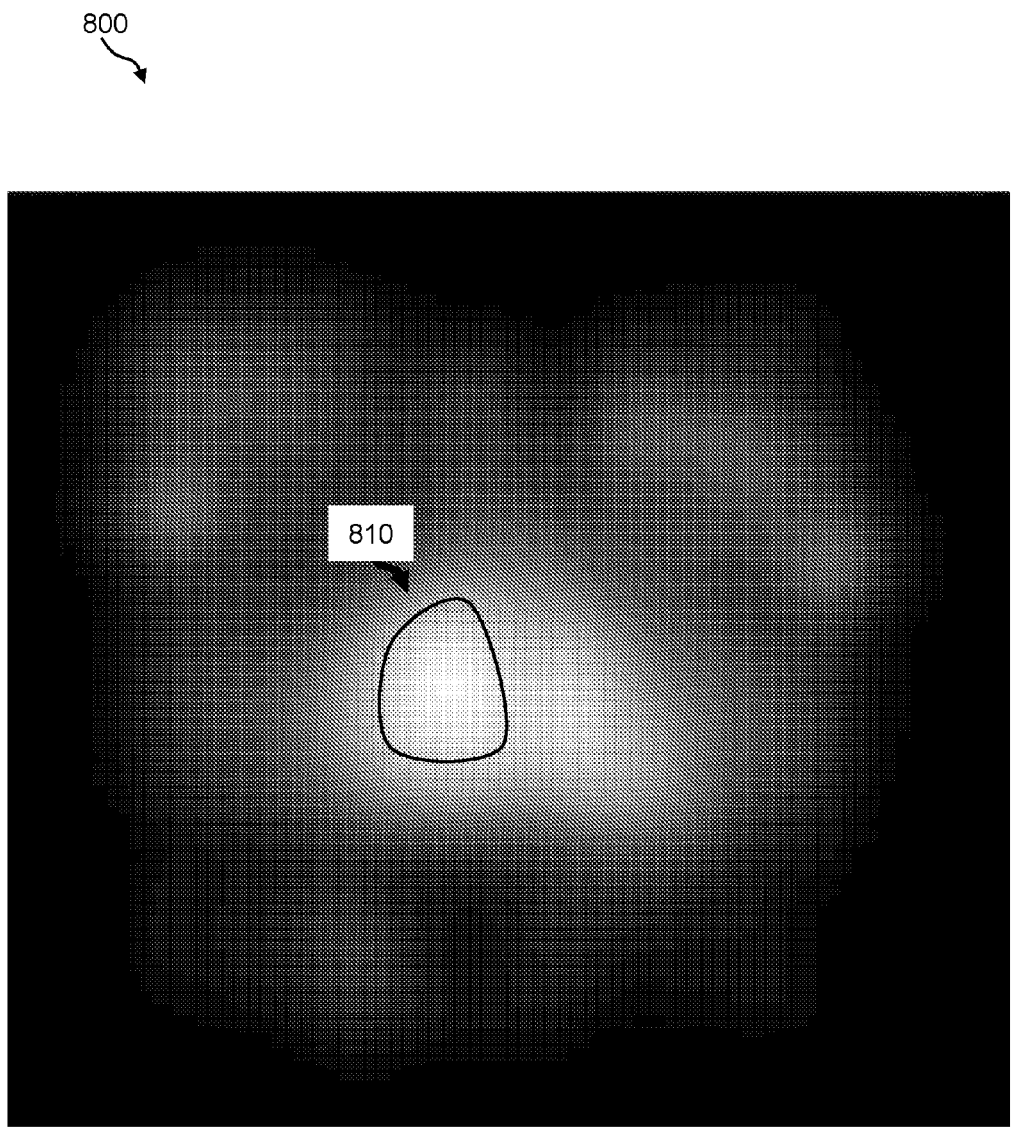
FIG. 8 is a depiction of an exemplary efflux rate constant map that can be acquired and processed using the image fusion process/processor of FIG. 3.

FIG. 8 provides an exemplary smoothed efflux rate constant map 800 that has been derived by computing efflux rate parameters from a contrast-enhanced dataset of the same prostate depicted in FIGS. 4-7. Using these maps, the image fusion process/processor 160 can provide a greater emphasis in tissues that exhibit high signal intensity values. In this example, the reader should note a cluster of pixels depicted by the reference numeral 810 that appear to be lightest relative to surrounding tissues. Cluster 810 appears to be the same potential tissue region of interest exhibiting a strong response in the ADC map 500 and the permeability map 600. Clearly, the clinician can benefit from a fusion image that directs attention to this region based on the plural responses exhibited in the parametric maps.

Other explicitly contemplated embodiments of parameters that can be computed by the parametric feature extraction processor 315 include, without limitation, time-to-peak parameters, contrast uptake or wash-in rate parameters, contrast washout rate parameters, peak enhancement parameters, slope parameters, and/or initial area under the contrast agent concentration curve (iAUC).

Other exemplary parametric values or features for extraction include morphological shape parameters in the form of a morphology map 322. While kinetic parameters characterize the motion of contrast agent in tissues, morphological parameters characterize the form or structure of the tissues. In one embodiment, morphologic shape parameters can be extracted by applying a Gaussian-based blob detection algorithm to pre-contrast, spatial pixel signal intensity values of the pre-processed, $T_2$-weighted medical image. Other explicitly contemplated embodiments of morphological maps or parameters include, without limitation, texture parameters for characterizing sharp or fuzzy edges of tissues.

In an embodiment, the image fusion process/processor 160 (FIG. 1) includes a scale normalizing process/processor 330 (FIG. 3) that normalizes input fusion parameters to a single scale. According to one embodiment, a pre-defined scale of 0 to 1 can be used by the processor, which emulates a probability range between 0 and 100%. That is, for every input parameter value, the scale normalizing processor provides a new output value in the range of 0 to 1. The conversion can be performed on a per-voxel level for all input fusion parameter values. The mechanism by which normalization occurs is highly variable. In general, normalization of a series if values entails analysis by the processor/process of the parameter's minima and maxima and thereafter applying a scalar that places the overall range of values within a normalized range that is acceptable to all images within the set being fused. In an embodiment, the scale normalizing process/processor ignores atypical observation values (e.g., above the 98th percentile, below the 2nd percentile) to ensure that outliers do not negatively affect the normalized values with respect to scale. The output from this process is illustratively shown as scale normalized parameter values 335.

In an embodiment, the image fusion process/processor 160 (FIG. 1) includes a response or probability value process/processor 340 (FIG. 3) that combines the scale-normalized parameter values to form final response values 345 that define the fused response image 166. In embodiments of a user-defined implementation of the fusion process, the user-defined parameters 172 are used as inputs in the computation of the final response value, which advantageously provides a more customized and intuitive fusion image to the reviewer. In embodiments of the region-based or "local" implementation of the fusion process, the scale-normalized parameter values are combined distinctively in accordance with the segmented organ zone in which they appear. For example, parameter values in the prostate peripheral zone can be weighted more heavily than the parameter values in the prostate central gland. In this embodiment, the response values are biased with a higher sensitivity towards regions of the tissues/organs where malignancies are more likely to appear. This biasing can be accomplished by applying a map of regions that includes predetermined information on the locations of such regions in a typical image. That is, where a region is likely to appear in a given portion of the image, that portion is flagged and the processed image is biased toward the corresponding region. Alternatively, pattern recognition or image processing applications can determine the location of the region or regions in which bias is to occur. In further embodiments of both user-defined and region-based implementations, clinicians are provided the flexibility of imposing region-specific biases to sequence- or parameter-specific image information. This can be accomplished by providing a region selection function in the user interface. The region selection function can include a menu or display of available regions, and selection buttons and/or slides (or other interface elements) that allow the selection of bias as well as the degree of bias.

The image fusion processor 160 illustratively utilizes either a linear or a non-linear function to compute the final response values 345. The fusion computation can be performed on a per-voxel basis and repeated for every voxel within the pre-processed image data, thereby creating a collection of response values suitable for implementation in the probability map 166.

Figure 9:
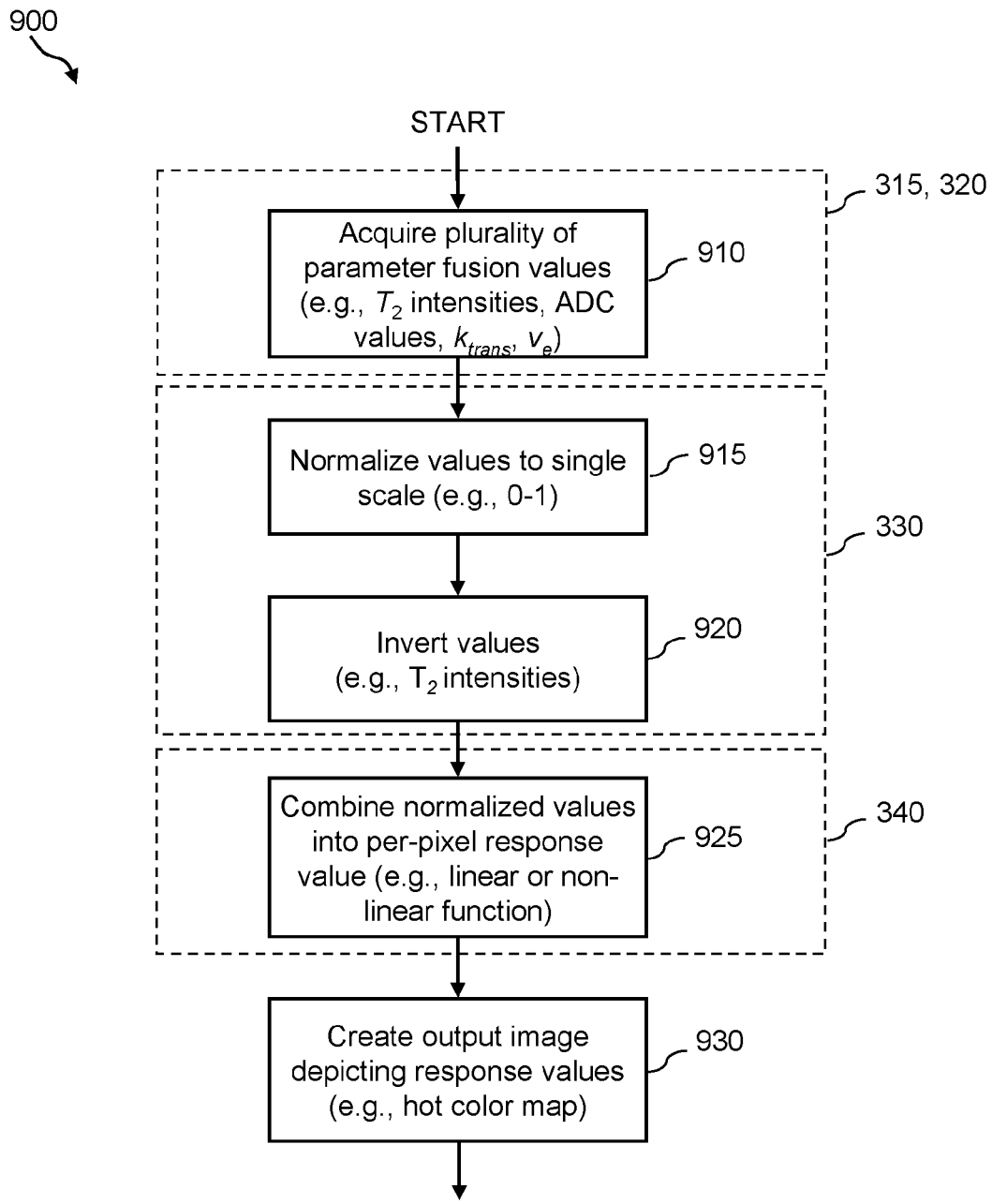
FIG. 9 is a flow diagram showing an illustrative runtime image fusion procedure for use with the image fusion process/processor of FIG. 3.

Reference is now made to an illustrative, multi-modal MR image fusion runtime procedure 900 as shown in FIG. 9. The various process steps in the procedure 900 have been grouped by dash-line boxes into a plurality of corresponding process/processors as described above with reference to FIG. 3, and associated reference numbers have been provided for each dashed-line box. It should be noted that the depicted steps can be arranged alternatively so that they are performed within a different process/processor, or performed in a discrete process/processor other than those described in FIG. 3.

At step 910, a plurality of parametric values to be fused is acquired. In this embodiment, the values include, on a per-voxel basis, $T_2$-weighted signal intensities, apparent diffusion coefficients, permeability parameters, and extracellular volume parameters. Illustratively, some values are acquired via the multi-modal parameter source 310, while some other values are computed by the parameter extraction processor 315.

Each discrete parameter value can potentially lie within a different range of values with respect to the other image parameter values. By way of example and without limitation, each voxel can have $T_2$-weighted signal intensity values ranging between 0 and 1,200, ADC values ranging between 0 and 5, extracellular volume values ranging between 0 and 1, and permeability values ranging between 0 and 2. At step 915 of the procedure 900, the values are converted to lie between an illustrative normalized scale of 0 to 1. Such steps can be performed by the scale normalizing process/processor 330, in an illustrative embodiment. For purposes of this description, each normalized set of values can be referred to at runtime as an "intermediate probability map" and illustrative examples of intermediate probability maps are depicted in FIGS. 4-8.

It is noted that, in certain parametric input data such as $T_2$-weighted signal intensities, as the intensity signal value of a voxel moves closer to 0, the voxel might be of a higher interest because low signal intensity values more frequently indicate tissue of interest (e.g., malignancies). At step 920, an inverse function is applied that transforms lower signal values into higher normalized probability values and vice versa. Such steps can also be illustratively performed by the scale normalizing process/processor 330. This step can be alternately performed prior to the scale normalization of the parameter values, in which case the inverted values are then normalized.

At step 925, a discrete map of response values is computed from the plurality of intermediate probability maps. Such steps are performed by the response value process/processor 340, in an illustrative embodiment. In certain embodiments, it is desirable to employ a linear function in the computation of the response values because the processing used by the system to derive the final probability map will become relatively intuitive to a clinician. That is, the clinician can readily comprehend the impact of each individual parameter value on the final response value. Furthermore, in embodiments of a user-defined implementation of the fusion process, the clinician can readily comprehend the impact that modifications to the user-defined parameters 172 will have on the response values.

An exemplary linear function for computing response values is shown by Equation 1:

$$\frac{\sum_i w_i P(m_i)}{\sum w_i} \quad \text{(Eq. 1)}$$

where $P(m_i)$ corresponds to a specific intermediate probability map of an image, and i and $W_i$ each correspond to a weight associated with $P(m_i)$.

In other embodiments, a non-linear function can be used to compute response values, in which the weighted probability maps are multiplied to compute a response value. An exemplary non-linear function for computing response values is shown by Equation 2:

$$\prod_i w_i P(m_i) \quad \text{(Eq. 2)}$$

At step 930 of the procedure 900, once response values are computed for each voxel, this data can be illustratively presented to the clinician in a raw image (e.g., by enhancing the intensities of a grayscale image in accordance with response values that indicate regions/voxels of interest), through a color map, or other conventional or novel visual presentation known to one of skill. In certain embodiments, a hot color map is formed and presented in which response values moving toward the range bound of 1 are colored red, values moving toward the opposing range bound of 0 are colored blue, and continuous values in between are colored with different shades that can conform with the spectrum or another appropriate color scale. Thus, it is expressly contemplated that the illustrative range bounds and associated colors are merely exemplary. Other choices could be implemented. It is further contemplated that voxels having response values below a cutoff threshold are not colored. The specific bounds, color intensities, color hues, and/or thresholds can also be specified as input parameters by the clinician via a system interface.

Figure 10:
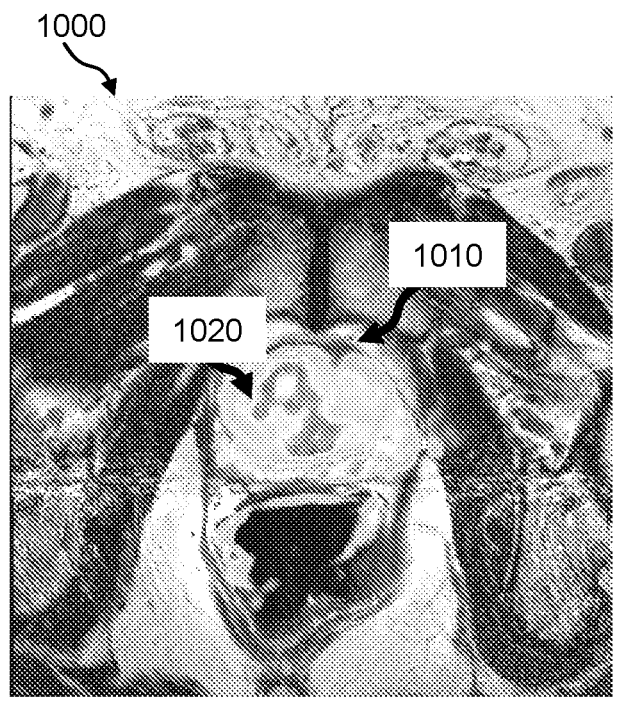
FIG. 10 is a depiction of an exemplary multi-parametric fusion image that can be generated and output using the image processing system of FIG. 1.

The results of a fusion process according to the system and method described herein are shown, by way of example in FIG. 10. The depicted fused response image provides a hot color map 1000 overlaid on an illustrative $T_2$-weighted prostate MR image 1010, although the hot color map could be presented as an overlay on a different image. The large (red) region 1020 signifies an area of concern in the subject prostate illustratively depicted in the parametric maps 400, 500, 600, 700, and 800. Thus, by providing a fusion of multiple images, each representing differing parameter sets, the clinician's attention is directed to areas of concern by consulting a single fused dataset. Moreover, the presentation of features in such areas is customized to reveal these features in a manner that most effectively assists the clinician in performing his or her analysis.

CONCLUSION

It should be clear that the system and method of the illustrative embodiments provide a fused magnetic resonance image that helps clinicians to more quickly and more accurately evaluate a significant amount of multi-modal MR image data information.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the system and method of the present invention, what has been described herein is merely illustrative of the application of the principles of the present invention. For example, some or all of the processes described herein can be implemented in hardware, software, including a computer-readable medium of program instructions, or a combination of hardware and software. Moreover, while images of an anatomical prostate have been presented to illustrate various aspects of the illustrative embodiments, such images should not be construed as limiting the utility of the present invention to any one particular organ or tissue. Accordingly, this description is meant to be taken only by way of example, and not to otherwise limit the scope of this invention.

What is claimed is:

1. A system for fusing and synthesizing a plurality of medical images defined by a plurality of imaging parameters comprising:
    an image fusion processor that fuses a plurality of magnetic resonance imaging (MRI) datasets, wherein a first image dataset of the MRI datasets is defined by apparent diffusion coefficient (ADC) values and a second image dataset of the MRI datasets is defined by at least one parameter other than the ADC values; and wherein the image fusion processor generates a fused response image that visually displays a combination of image features generated by the ADC values combined with image features generated by the at least one parameter other than the ADC values.

2. The system as set forth in claim 1 wherein the at least one parameter comprises a parameter based upon at least one of a $T_2$-weighted medical image and dynamic contrast enhanced MRI (DCE-MRI) medical image.

3. The system as set forth in claim 1 further comprising a registration processor that aligns each of the first image data set and the second image dataset into a registered multi-modal image dataset.

4. The system as set forth in claim 3 wherein the registration processor includes a non-rigid registration processor and an atlas/template registration processor that operates upon the image data based upon atlas coordinate data related to imaged tissue.

5. The system as set forth in claim 4 further comprising a segmentation processor that applies the atlas coordinate data to the registered multi-modal image dataset to generate segmented organ/tissue image data with respect to regions of interest in the multi-modal image dataset.

6. The system as set forth in claim 3 further comprising an intensity homogeneity correction processor that generates a homogeneous organ/tissue image dataset by smoothing and filtering image intensities with respect to the organ/tissue image data.

7. The system as set forth in claim 1 wherein the fusion processor receives inputs of user-defined parameters to vary image data displayed in the fused response image in accordance with the user's desired criteria.

8. The system as set forth in claim 7 wherein the fusion processor includes (a) a scale normalizing processor that receives map data from a multi-modal parameter source and generates scale-normalized parameter values and (b) a response processor that generates response values that define the fused response image.

9. The system as set forth in claim 1 wherein the fused response image includes at least one of color-enhanced regions of interest and intensity-enhanced regions of interest.

10. A method for fusing and synthesizing a plurality of medical images defined by a plurality of imaging parameters comprising the steps of:

fusing a plurality of magnetic resonance imaging (MRI) datasets, in which a first image dataset of the MRI datasets is defined by apparent diffusion coefficient (ADC) values and a second image dataset of the MRI datasets is defined by at least one parameter other than the ADC values; and generating a fused response image that visually displays a combination of image features generated by the ADC values combined with image features generated by the at least one parameter other than the ADC values.

11. The method as set forth in claim 10 wherein the at least one parameter comprises a parameter based upon at least one of a $T_2$-weighted medical image and dynamic contrast enhanced MRI (DCE-MRI) medical image.

12. The method as set forth in claim 10 further comprising aligning each of the first image data set and the second image dataset into a registered multi-modal image dataset.

13. The method as set forth in claim 12 wherein the step of aligning includes operating upon the image data based upon atlas coordinate data related to imaged tissue.

14. The method as set forth in claim 13 further comprising applying the atlas coordinate data to the aligned multi-modal image dataset to generate segmented organ/tissue image data with respect to regions of interest in the multi-modal image dataset.

15. The method as set forth in claim 12 further comprising generating a homogeneous organ/tissue image dataset by smoothing and filtering image intensities with respect to the organ/tissue image data.

16. The method as set forth in claim 10 wherein the step of generating the fused response image includes receiving inputs of user-defined parameters to vary image data displayed in the fused response image in accordance with the user's desired criteria.

17. The method as set forth in claim 10 wherein the step of generating the fused response image includes (a) receiving map data from a multi-modal parameter source and generating scale-normalized parameter values and (b) generating response values that define the fused response image.

18. The method as set forth in claim 10 wherein the fused response image includes at least one of color-enhanced regions of interest and intensity-enhanced regions of interest.

* * * * *